(12) United States Patent
Gerhart et al.

(10) Patent No.: US 8,175,679 B2
(45) Date of Patent: May 8, 2012

(54) CATHETER ELECTRODE THAT CAN SIMULTANEOUSLY EMIT ELECTRICAL ENERGY AND FACILITATE VISUALIZATION BY MAGNETIC RESONANCE IMAGING

(75) Inventors: John P. Gerhart, Plymouth, MN (US); Harry Puryear, Shoreview, MN (US); Jeremy D. Dando, Plymouth, MN (US); Scott R. Petersen, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1167 days.

(21) Appl. No.: 11/964,194

(22) Filed: Dec. 26, 2007

(65) Prior Publication Data

US 2009/0171187 A1 Jul. 2, 2009

(51) Int. Cl.
*A61B 18/18* (2006.01)

(52) U.S. Cl. ......... 600/423; 600/424; 600/427; 604/22; 607/101; 607/122

(58) Field of Classification Search .................. 600/411, 600/422, 423; 607/5, 6, 2, 100, 101, 113, 607/116, 122, 127; 606/27, 32, 41
See application file for complete search history.

(56) References Cited

U.S. PATENT DOCUMENTS

| | | | |
|---|---|---|---|
| 4,572,198 A | 2/1986 | Codrington | |
| 4,960,106 A * | 10/1990 | Kubokawa et al. | 600/104 |
| 5,143,090 A | 9/1992 | Dutcher | |
| 5,271,400 A | 12/1993 | Dumoulin et al. | |
| 5,307,808 A | 5/1994 | Dumoulin et al. | |
| 5,318,025 A | 6/1994 | Dumoulin et al. | |
| 5,391,199 A | 2/1995 | Ben-Haim | |
| 5,443,489 A | 8/1995 | Ben-Haim | |
| 5,715,822 A | 2/1998 | Watkins et al. | |
| 5,769,843 A | 6/1998 | Abela et al. | |
| 5,846,198 A | 12/1998 | Killmann | |
| 5,868,674 A | 2/1999 | Glowinski et al. | |
| 5,916,162 A | 6/1999 | Snelten | |
| 5,938,603 A | 8/1999 | Ponzi | |
| 5,954,665 A | 9/1999 | Ben-Haim | |
| 6,016,439 A | 1/2000 | Acker | |

(Continued)

FOREIGN PATENT DOCUMENTS

WO 00/25672 5/2000

(Continued)

OTHER PUBLICATIONS

Alford, Superconducting Receive Coils for a Compact Low Field MRI System, http://ecce1.1sbu.ac.uk/research/pem/MRI.html.

(Continued)

*Primary Examiner* — Parikha Mehta
(74) *Attorney, Agent, or Firm* — Dykema Gossett PLLC

(57) ABSTRACT

An electrode for use on a medical device is disclosed. The electrode may have a main body of electrically conductive material extending along an axis and having a proximal end and a distal end. The body may be configured to emit electrical energy in accordance with a predefined diagnostic or therapeutic function. The body may have a groove disposed over an outermost surface of the body. The electrode may also include a magnetic resonance imaging (MRI) tracking coil disposed in said groove. The MRI tracking coil may comprise electrically insulated wire, for example. A catheter including an electrode, as well as a method for determining the location of an electrode, are also disclosed.

34 Claims, 4 Drawing Sheets

U.S. PATENT DOCUMENTS

| | | |
|---|---|---|
| 6,171,240 B1 * | 1/2001 | Young et al. .......... 600/410 |
| 6,185,448 B1 | 2/2001 | Borovsky |
| 6,226,432 B1 | 5/2001 | Gonda et al. |
| 6,226,543 B1 | 5/2001 | Gilboa et al. |
| 6,241,724 B1 | 6/2001 | Fleischman et al. |
| 6,246,896 B1 | 6/2001 | Dumoulin et al. |
| 6,275,721 B1 | 8/2001 | Darrow et al. |
| 6,289,233 B1 | 9/2001 | Dumoulin et al. |
| 6,377,048 B1 | 4/2002 | Golan et al. |
| 6,569,160 B1 | 5/2003 | Goldin et al. |
| 6,593,884 B1 | 7/2003 | Gilboa et al. |
| 6,600,319 B2 | 7/2003 | Golan |
| 6,642,297 B1 | 11/2003 | Hyatt |
| 6,701,176 B1 | 3/2004 | Halperin et al. |
| 6,704,594 B1 | 3/2004 | Blank et al. |
| 6,736,704 B2 | 5/2004 | Kennedy |
| 6,749,571 B2 | 6/2004 | Varghese |
| 6,862,468 B2 | 3/2005 | Smith |
| 6,904,307 B2 | 6/2005 | Karmarkar |
| 6,932,813 B2 | 8/2005 | Thompson et al. |
| 6,968,236 B2 | 11/2005 | Hagele |
| 7,048,716 B1 | 5/2006 | Kucharczyk |
| 7,155,271 B2 | 12/2006 | Halperin |
| 7,166,075 B2 | 1/2007 | Varghese |
| 7,250,049 B2 | 7/2007 | Roop et al. |
| 7,264,619 B2 | 9/2007 | Venturelli |
| 7,289,839 B2 | 10/2007 | Dimmer |
| 2003/0050557 A1 | 3/2003 | Susil |
| 2003/0208252 A1 | 11/2003 | O'Boyle |
| 2003/0236456 A1 | 12/2003 | Graham |
| 2004/0116800 A1 | 6/2004 | Helfer |
| 2004/0116801 A1 | 6/2004 | Konings |
| 2004/0220470 A1 | 11/2004 | Karmarkar et al. |
| 2004/0230114 A1 | 11/2004 | Clatterbaugh et al. |
| 2005/0014995 A1 | 1/2005 | Amundson |
| 2005/0054914 A1 | 3/2005 | Duerk et al. |
| 2005/0070972 A1 | 3/2005 | Wahlstrand |
| 2005/0102006 A1 | 5/2005 | Whitehurst |
| 2005/0171427 A1 | 8/2005 | Nevo et al. |
| 2005/0215886 A1 | 9/2005 | Schmidt |
| 2005/0215899 A1 | 9/2005 | Trahey et al. |
| 2005/0261569 A1 | 11/2005 | Schulz |
| 2005/0261571 A1 | 11/2005 | Willis |
| 2006/0030844 A1 | 2/2006 | Knight |
| 2006/0084861 A1 | 4/2006 | Blank et al. |
| 2006/0084866 A1 | 4/2006 | Lewkonya |
| 2006/0100506 A1 | 5/2006 | Halperin |
| 2006/0118319 A1 | 6/2006 | Wang |
| 2006/0135961 A1 | 6/2006 | Rosenman |
| 2006/0229659 A1 | 10/2006 | Gifford |
| 2007/0066972 A1 * | 3/2007 | Ormsby et al. .......... 606/41 |
| 2007/0078457 A1 | 4/2007 | Paul et al. |
| 2007/0088244 A1 | 4/2007 | Millet |
| 2007/0088416 A1 | 4/2007 | Atalar |
| 2007/0100240 A1 | 5/2007 | Hiltawski |
| 2007/0106148 A1 | 5/2007 | Dumoulin |
| 2007/0123764 A1 | 5/2007 | Thao et al. |
| 2007/0156205 A1 | 7/2007 | Larson et al. |
| 2007/0167705 A1 | 7/2007 | Chiang |
| 2007/0255132 A1 | 11/2007 | Shalgi |
| 2007/0282301 A1 | 12/2007 | Segalescu |
| 2007/0293754 A1 | 12/2007 | Schneid |
| 2008/0009700 A1 | 1/2008 | Dumoulin |
| 2008/0021308 A1 | 1/2008 | Dimmer |
| 2008/0033417 A1 | 2/2008 | Nields |
| 2008/0033418 A1 | 2/2008 | Nields |
| 2008/0033419 A1 | 2/2008 | Nields |
| 2008/0033420 A1 | 2/2008 | Nields |
| 2008/0038146 A1 | 2/2008 | Wachter |
| 2008/0045908 A1 | 2/2008 | Gould |

FOREIGN PATENT DOCUMENTS

| | | |
|---|---|---|
| WO | 2004/068947 A2 | 8/2004 |
| WO | 2004/113945 A2 | 12/2004 |

OTHER PUBLICATIONS

Beals, New Brain-Imaging Technique Detects Early Stages of MCI, AD, Alzheimer's Association 2007 International Conference on Prevention of Dementia: Abstract P-231, presented Jun. 11, 2007.

Lederman, Cardiovascular Interventional MRI, Circulation, Nov. 8, 2005; 112(19):3009-3017.

Rutt, An Expandable Intravenous RF Coil for Arterial Wall Imaging, Journal of Magnetic Resonance Imaging, 8:226-234, 1998, http://www.imaging.robarts.ca/~brutt/Research/arterial.html.

Wacker et al., The Catheter-Driven MRI Scanner: A New Approach to Intravascular Catheter Tracking and Imaging-Parameter Adjustment for Interventional MRI, American Journal of Roentgenology: 183, Aug. 2004.

Weaver et al., Magnetic Resonance Elastography Using 3D Gradient Echo Measurements of Steady-State Motion, Medical Physics, vol. 28, No. 8, Aug. 2001.

Emerging Device Technology: MRI Coils, University of Birmingham, http://www.edt.bham.ac.uk/mri.htm.

Magnetic Resonance Elastography; http://india.cchem.berkeley.edu/~vdemas/Elastography.htm.

MR Elastography Quantitatively Assesses Liver Fibrosis, Reuters Health Information 2006; Radiology 2006; 240:440-448, http://www.medscape.com/viewarticle/544969.

The Walsworth Group (Harvard-Smithsonian Center for Astrophysics; Harvard University Department of Physics), Photos of the Week from 2006, Dec. 19, 2006, www.cfa.harvard.edu/Walsworth/Activities/Photo_of_Week2006.html.

International Search Report and Written Opinion in PCT/US2008/084203 mailed Feb. 4, 2009.

U.S. Appl. No. 11/966,576, filed Dec. 28, 2007 for Flexible Polymer Electrode for MRI-Guided Positioning and Radio Frequency Ablation.

* cited by examiner

CATHETER ELECTRODE THAT CAN SIMULTANEOUSLY EMIT ELECTRICAL ENERGY AND FACILITATE VISUALIZATION BY MAGNETIC RESONANCE IMAGING

BACKGROUND OF THE INVENTION a. Field of the Invention

The instant invention is directed toward an electrode for a catheter, including an electrode that may simultaneously emit electrical energy and facilitate visualization by magnetic resonance imaging (MRI).

b. Background Art

Catheters have been in use for medical procedures for many years. Catheters can be used for medical procedures to examine, diagnose, and treat while positioned at a specific location within a body that is otherwise inaccessible without more invasive procedures. During these procedures a catheter is commonly inserted into a vessel near the surface of the body and is guided to a specific location within the body for examination, diagnosis, and/or treatment. For example, one procedure often referred to as "catheter ablation" utilizes a catheter to convey an electrical stimulus to a selected location within the human body to create tissue necrosis. Another procedure often referred to as "mapping" utilizes a catheter with sensing electrodes to monitor various forms of electrical activity in the human body.

Catheters are also used for medical procedures involving the human heart. Typically, the catheter is inserted in an artery or vein in the leg, neck, or arm of the patient and directed, sometimes with the aid of a guide wire or introducer, through the vessels until an electrode of the catheter reaches the desired location for the medical procedure in the heart.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes. Mapping catheters also often contain a plurality of sensing electrodes to monitor various forms of electrical activity in the human body.

An application may be utilized to create images of the catheter's surroundings. Images may be acquired through visible light, ultrasound, or magnetic resonance (MR). The application may be used to acquire high resolution radiographic images of tissue surrounding the catheter, for example, the acquisition of high resolution magnetic resonance images of blood vessel walls for the visualization and differentiation of various types of tissues and plaques.

Magnetic resonance imaging (MRI) may also be employed during a medical procedure to assist a physician in guiding a catheter and/or a portion of a catheter, such as an electrode. For example, tracking devices may be attached to a catheter (or other medical device) to be tracked. The tracking device may comprise a coil (e.g., induction coil). An MR pulse sequence may be performed where the coil is used to acquire a signal which indicates the location of the tracked device (e.g., catheter). The location of the coil may be determined and superimposed at the corresponding location in a medical image acquired with an MR imaging system.

Conventional designs for catheters for MRI-guided electrode positioning may rely on a plurality of tracking devices placed at discrete locations along the longitudinal axis of the catheter shaft. The tracking devices may be located on the shaft proximal to an electrode. The tracking devices may be utilized to sense and indicate the location and orientation of the catheter within a body through a control system. The control system may also be used to control a set of imaging coils to image selective areas of the body cavity and/or to control the amount of energy applied to electrodes (e.g., ablation elements) on the catheter to treat target tissue. The energy may cause heating, and at certain temperatures, tissue cells may be destroyed. A plurality of tracking devices may be required in order to provide information regarding the flex of the catheter shaft. Conventional designs may utilize a plurality of tracking devices on the catheter shaft itself, taking up valuable space on the catheter shaft. The plurality of tracking coils may be used to create a linear vector for approximating the location of the electrode at the distal end of the catheter shaft. In other circumstances, the tracking devices may also be used to compute the curve of the shaft as an interpolated polynomial, such as a cubic spline. The computed curve may then be extrapolated to estimate the projected location of the electrode at the distal end of the catheter shaft. The location of the electrode at the distal end of the catheter shaft may thus be an indirectly computed estimate, not a directly measured value.

Thus, there remains a need for an apparatus and method for directly measuring the location of an electrode disposed on a catheter (e.g., the electrode disposed at the distal tip of a catheter) without having to resort to extrapolation or estimation. There also remains a need for a apparatus and method for providing information regarding the flex of a catheter without having to place multiple tracking devices on the catheter shaft itself.

BRIEF SUMMARY OF THE INVENTION

It is desirable to provide an electrode that may be configured for compatibility with MR imaging applications to provide a direct measurement of the location of the electrode at the distal end of a catheter shaft, while retaining the electrical, thermal, and mechanical properties of conventional electrodes. It may also be desirable to decrease the number of tracking devices placed on the shaft of a catheter, while retaining the ability to measure the flex of a catheter.

An electrode for use on a medical device is disclosed. The electrode may have a main body of electrically conductive material extending along an axis and having a proximal end and a distal end. The body may be configured to emit electrical energy in accordance with a predefined diagnostic or therapeutic function. The body may have a groove disposed over an outermost surface of the body. The electrode may also include a magnetic resonance imaging (MRI) tracking coil disposed in the groove. The MRI tracking coil may comprise electrically insulated wire, for example. A catheter including an electrode, as well as a method for determining the location of an electrode, are also disclosed.

The catheter may include a shaft and an electrode disposed on the shaft. The electrode may have a main body of electrically conductive material extending along an axis and having a proximal end and a distal end. The body may have a groove disposed over an outermost surface of the body. The electrode may also include a magnetic resonance imaging (MRI) tracking coil disposed in the groove. The MRI tracking coil may comprise electrically insulated wire, for example. The catheter may further include an MRI receiving coil configured for MRI imaging disposed in the shaft proximate the electrode.

A method of determining the location of an electrode may comprise the steps of: providing an electrode having a main body of electrically conductive material extending along an axis and having a proximal end and a distal end; forming a groove in an outermost surface of the body; and disposing a magnetic resonance imaging (MRI) tracking coil in the groove. The tracking coil may comprise electrically insulated wire, for example. The method may further include the step of receiving an induced signal developed in the MRI tracking coil at a magnetic resonance imaging (MRI) system input.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
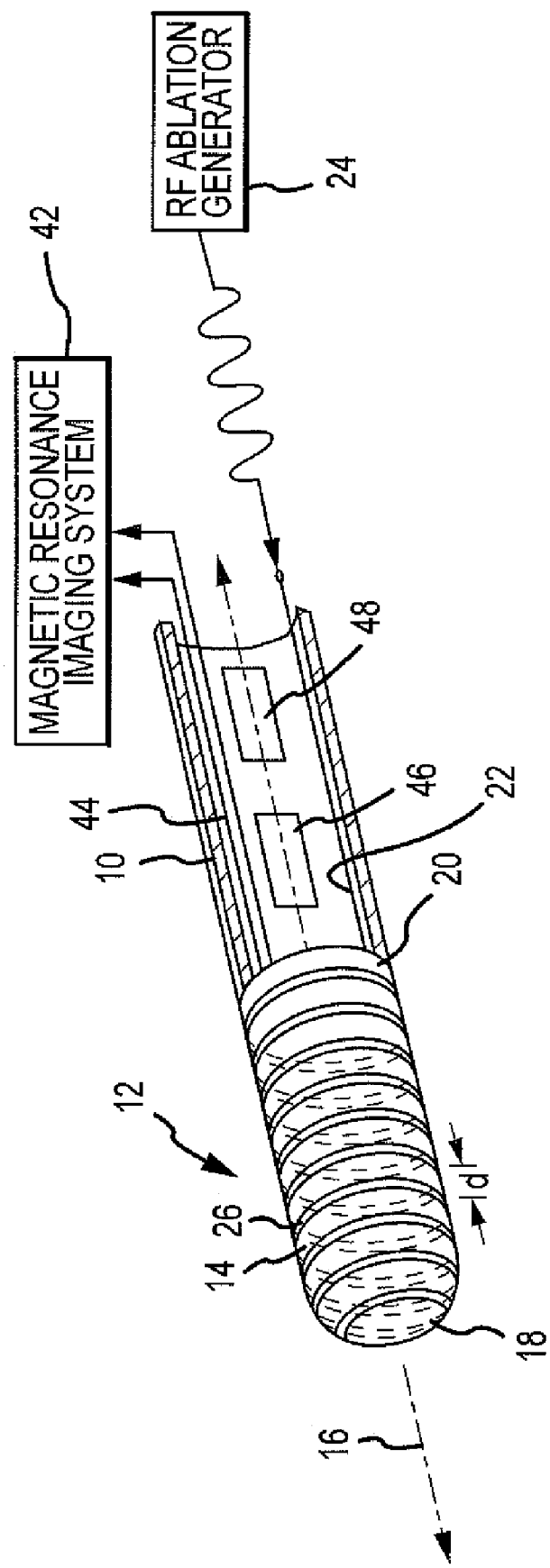
FIG. 1 is a partial, simplified, cross-sectional view of a catheter including a shaft with an electrode in accordance with a first embodiment of the invention.

FIG. 1 illustrates a partial, simplified side view of a catheter including a shaft 10 with an electrode 12 in accordance with an embodiment of the invention. Shaft 10 may be designed for insertion into a main lumen of a sheath for eventual insertion into the body of a patient. Shaft 10 may comprise one or a plurality of layers. For example and without limitation, shaft 10 may comprise a braided layer of metal wire for additional stability and one or more layers of polymeric materials to create the desired stiffness and/or flexibility for the catheter. Shaft 10 may define one or more lumens for electrical leads, steering wires, or various other items that may be utilized within shaft 10. Shaft 10 may include a proximal section and a distal section. As used herein, "proximal" generally refers to a direction away from the body of a patient and toward a clinician. In contrast, "distal" generally refers to a direction toward the body of the patient and away from the clinician. While electrode 12 may be disclosed and described in connection with a catheter, the use of a catheter is for illustration purposes only, and electrode 12 may also be utilized in connection with other medical devices.

Electrode 12 may be mechanically connected (e.g., attached) to the distal section of shaft 10. Although electrode 12 is described as connected to the distal section of shaft 10, an electrode 12 may be connected to one or more other locations along shaft 10 in other embodiments. Electrode 12 may be configured to emit electrical energy in accordance with a predefined diagnostic or therapeutic function. For example, the predefined diagnostic or therapeutic function may include radio frequency (RF ablation). Electrode 12 may have the electrical, thermal, and mechanical properties required of an electrode used for RF ablation. For example, at least a portion of electrode 12 may comprise an electrically conductive material. In an embodiment, electrode 12 may comprise a main body 14 extending along an axis 16. Body 14 of electrode 12 may have a distal end 18 and a proximal end 20. Body 14 of electrode 12 may be generally cylindrical in shape.

Although a cylindrical shape is described and illustrated, electrode 12 may be formed in other shapes. Distal end 18 may include a rounded tip. Distal end 18 may be rounded so as to minimize irritation to the body cavity into which a medical device including the electrode 12 may be inserted.

Body 14 of electrode 12 may be solid in an embodiment. At least a portion of body 14 may comprise an electrically conductive material. At least a portion of body 14 may comprise a non-ferrous material or a material that is non-magnetically responsive (e.g., has a magnetic susceptibility less than $1 \times 10^{-4}$). Magnetic susceptibility may refer to the degree of magnetization of a material (e.g., the extent that the material is affected by a magnetic field) in response to a magnetic field. For example, body 14 may comprise gold, silver, platinum, iridium, titanium, tungsten or a combination thereof. In an embodiment, body 14 may comprise a material with magnetic susceptibility properties that are substantially similar to human tissue. For example and without limitation, body 14 may comprise a gold alloy. A gold alloy may closely reflect the properties of human tissue (e.g. have a magnetic susceptibility that is substantially similar to human tissue). In particular, a gold alloy may more closely reflect the properties of human tissue than pure gold. When body 14 comprises a material closely reflecting the properties of human tissue, the use of electrode 12 for MRI-guided application may be improved.

As described above, electrode 12 may be configured for imparting (e.g., emitting) energy (e.g., RF energy) to target tissue. An electrical conductor 22 may be configured to carry ablative energy (e.g. RF current) from an energy source in a controller (not shown) to electrode 12. Electrical conductor 22 may have a first end coupled to body 14 of electrode 12. Electrical conductor 22 may have a second end configured for connection to an energy source 24. Energy source 24 may comprise a radio frequency ablation generator in an embodiment. Electrical conductor 22 may extend within shaft 10 along axis 16. Electrical conductor 22 may comprise an electrically conductive wire. For example, and without limitation, electrical conductor 22 may comprise copper wire. Electrical conductor 22 may have an uninsulated portion for electrical contact with electrode 12. For example, the first end (e.g., a distal end) of electrical conductor 22 may be uninsulated. The first end of electrical conductor 22 may be electrically coupled to proximal end 20 of body 14 at a single point (e.g., a point connection). At least a portion of the remainder of electrical conductor 22 may be electrically insulated. For example, the portion of electrical conductor 22 extending along shaft 10 outside of electrode 12 may be electrically insulated.

Figure 2:
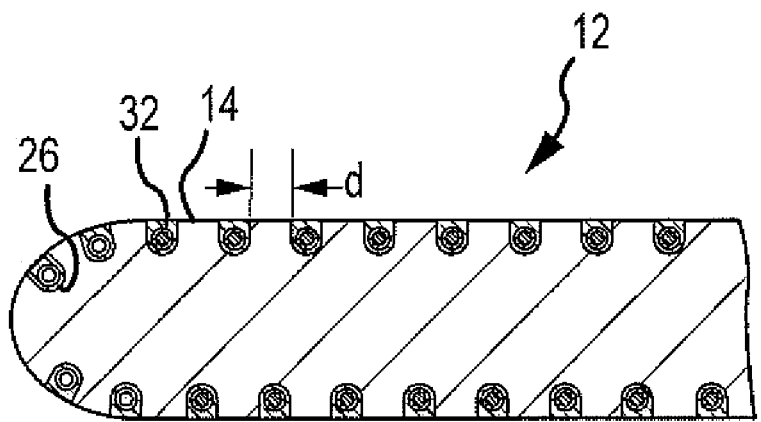
FIG. 2 is a longitudinal, simplified, cross-sectional view of the electrode of FIG. 1 in accordance with a first embodiment of the invention.
Figure 3:
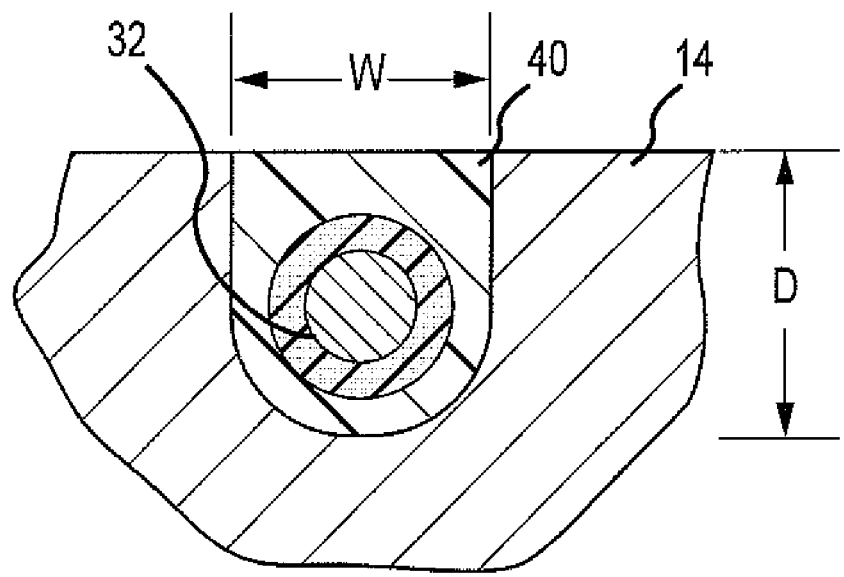
FIG. 3 is an enlarged, cross-sectional view of the electrode of FIG. 2, with portions broken away.

Body 14 of electrode 12 may include a groove disposed over an outermost surface of body 14. Referring now to FIGS. 1-3, the groove may comprise a continuous spiral niche 26 in a first embodiment. Spiral niche 26 may include an entry and an exit and may extend a predetermined number of turns from the entry to the exit. For example and without limitation, the predetermined number of turns of spiral niche 26 may be approximately 10 turns. The distance d between adjacent turns may be constant along the axial length of body 14. For example and without limitation, the distance d between adjacent turns may be equal to or less than about 0.5 mm. Spiral niche 26 may have a width W equal to or less than about 0.5 mm. Spiral niche 26 may have a width equal to or less than about 0.5 mm in order to help avoid creating gaps in the areas targeted for ablation which may disrupt lesion formation. In particular, by maintaining a width W that is equal to or less than about 0.5 mm, the entire tissue targeted for ablation by electrode 12 may be adequately and/or sufficiently ablated without gaps occurring in the area where spiral niche 26 was located. Spiral niche 26 may have a width substantially corresponding to a diameter of the wire making up a tracking device (described below). Spiral niche 26 may also have a depth D in the radial direction that is sufficient to receive the tracking device so that the tracking device is not disposed externally to the outermost surface of body 14 of electrode 12.

Figure 4:
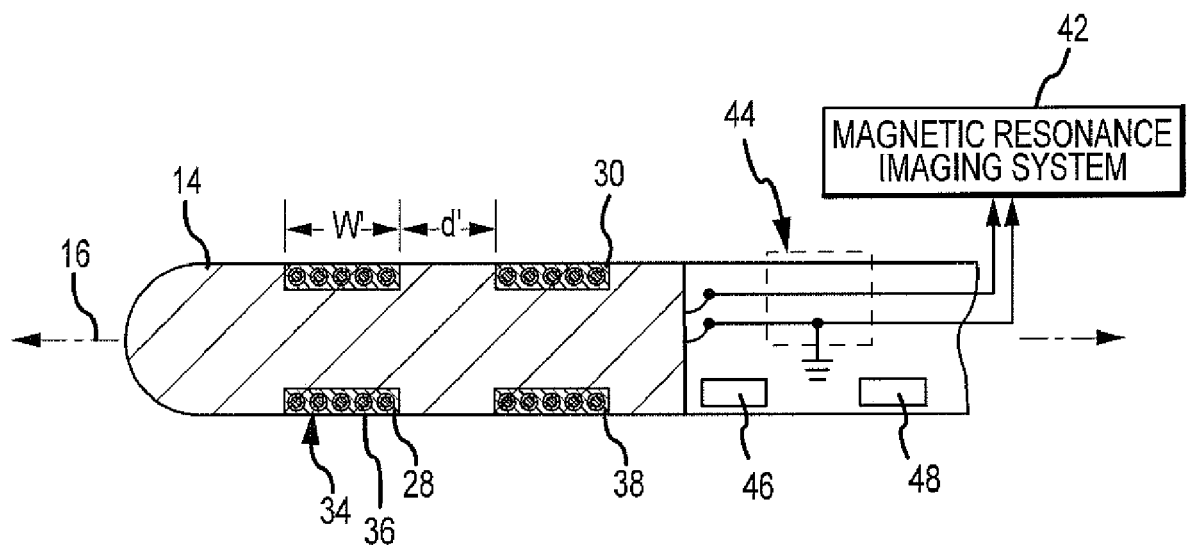
FIG. 4 is a partial, simplified, longitudinal, cross-sectional view of an electrode in accordance with a second embodiment of the invention.
Figure 5:
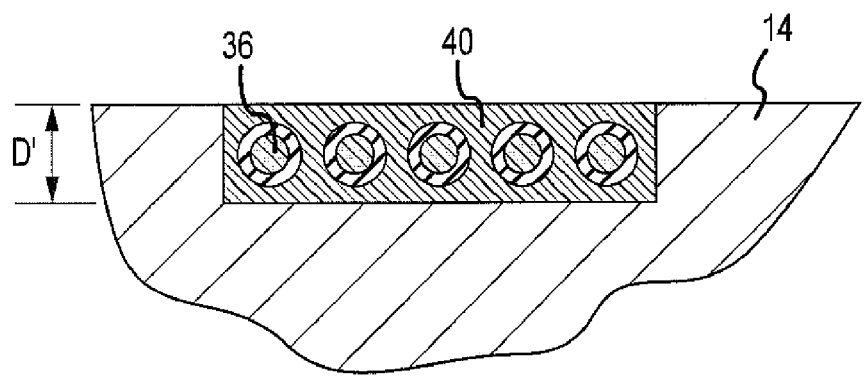
FIG. 5 is an enlarged, cross-sectional view of the electrode of FIG. 4, with portions broken away.

Referring now to FIGS. 4-5, in a preferred embodiment the groove may comprise a channel 28 extending radially inwardly from an outermost surface of body 14. The groove may comprise a single channel that may extend radially inwardly from an outermost surface of body 14. The single channel may be large enough to house an entire tracking device. As illustrated, the groove may comprise a first channel 28 and a second channel 30. The groove may comprise fewer or more channels in other embodiments. Both first and second channels 28, 30 may extend radially inwardly from an outermost surface of body 14. First channel 28 may be axially offset or spaced apart from second channel 30 by a predetermined distance d'. For example and without limitation, the predetermined distance d' may be about 0.5 mm. First and second channels 28, 30 may each have a width W' equal to or less than about 0.5 mm. Width W' may extend along axis 16. As in connection with the first embodiment, first and second channels 28, 30 may have a width equal to or less than about 0.5 mm in order to help avoid creating gaps in the areas targeted for ablation which may disrupt lesion formation. In particular, by maintaining a width W' that is equal to or less than about 0.5 mm, the entire tissue targeted for ablation by electrode 12 may be adequately and/or sufficiently ablated without gaps occurring in the area where first channel 28 and/or second channel 30 were located. First and second channels 28, 30 may have a width W' that is substantially larger than the diameter of the wire making up tracking device (described below). First and second channels 28, 30 may also have a depth D' that is sufficient to receive the tracking device so that the tracking device is not exposed externally to the outermost surface of body 14 of electrode 12. First and second channels 28, 30 may have a width of axial length W' (e.g., along axis 16) that is substantially larger than a depth D' in the radial direction.

Electrode 12 may be configured for compatibility with MRI-guided applications. Accordingly, electrode 12 may include a magnetic resonance imaging (MRI) tracking coil 32 or 34. MRI tracking coil 32 or 34 may be wound in a substantially cylindrical shape and may have a longitudinal axis that is coincident with axis 16 of body 14. MRI tracking coil 32 (see FIGS. 2-3) or 34 (see FIGS. 4-5) may comprise an electrically insulated wire capable of carrying the current required to create a coil signal. MRI tracking coil 32 or 34 may function as an RF antenna typically used in interventional MRI applications, and accordingly will be formed having a predetermined number of turns to ensure adequate performance, in view of the various other portions of the MRI system with which it will be required to interact. Referring now to the embodiment illustrated in FIGS. 1-3, MRI tracking coil 32 may have a single segment with a predetermined number of turns. For example and without limitation, the predetermined number of turns in the segment may be approximately 10 turns. The distance between adjacent turns may be constant along the axial length of body 14. For example and without limitation, the distance between adjacent turns may be equal to or less than about 0.5 mm. MRI tracking coil 32 may be disposed in spiral niche 26 in an embodiment. The electrically insulated wire comprising MRI tracking coil 32 may be at least 0.02 mm in diameter in an embodiment, and preferably about 0.1 mm in diameter.

Referring now to the preferred embodiment illustrated in FIGS. 4-5, MRI tracking coil 34 may comprise a first segment 36 with a first predetermined number of turns and a second segment 38 with a second predetermined number of turns. For example and without limitation, the first and second predetermined number of turns in each segment 36, 38 may be approximately five turns. The distance between adjacent turns in each segment 36, 38 may be constant along the axial length of body 14. For example and without limitation, the distance between adjacent turns in each segment 36, 38 may be equal to or less than about 0.5 mm. The first segment 36 may be disposed in first channel 28 in an embodiment, and the second segment 38 may be disposed in second channel 30 in an embodiment. The first and second segments 36, 38 may be axially offset or spaced apart by a predetermined distance d'. For example and without limitation, the predetermined distance d' may be about 0.5 mm. Each segment 36, 38 may have an axial length equal to or less than about 0.5 mm. The electrically insulated wire comprising MRI tracking coil 34 may be at least 0.02 mm in diameter in an embodiment, and preferably about 0.1 mm in diameter. The first and second segments may be electrically series-connected in an embodiment.

As described above, the groove disposed in the outermost surface of body 14 may have a depth that is sufficient to receive MRI tracking coil 32 or 34 so that the MRI tracking coil 32 or 34 is not exposed externally to the outermost surface of body 14 of electrode 12. In an embodiment, an electrically conductive polymer 40 may be disposed in the groove to fill the gap between the MRI tracking coil 32 or 34 and the outermost surface of body 14. For example, electrically conductive polymer 40 may be disposed in the groove so that an outermost surface of polymer 40 is substantially flush with an outermost surface of body 14 of the electrode 12. For example and without limitation, polymer 40 may comprise a silicone material. Polymer 40 may have electrically conductive particles dispersed therein at a predefined density. The density of the electrically conductive particles may be defined to achieve a desired electrical conductivity. The electrically conductive particles may comprise metal particles in an embodiment. For example and without limitation, the electrically conductive particles may comprise gold.

An MR pulse sequence may be performed using MRI tracking coil 32 or 34 to develop an induced signal configured for use by a magnetic resonance imaging (MRI) system 42. For example, an electromagnetic force (EMF) may be induced in the MRI tracking coil 32 or 34 as would be understood by one of ordinary skill in the art. The induced signal may have sufficient information encoded therewith to be indicative of a position or a location of electrode 12. The MRI system 42 may be responsive to the induced signal from MRI tracking coil 32 or 34 to depict a location of electrode 12 in a patient. For example, MRI system 42 may utilize the induced signal to render a graphic display of the position or location of electrode 12. In an embodiment, another electrical conductor 44 may carry the induced signal from MRI tracking coil 32 or 34 to MRI system 42. Electrical conductor 44 may be configured for connection to MRI tracking coil 32 or 34. Electrical conductor 44 may extend within catheter shaft 10 along axis 14 of electrode 12. In an embodiment, electrical conductor 44 may comprise a micro-coaxial cable.

Catheter shaft 10 may further comprise an MRI receiving coil 46 configured for MRI imaging in an embodiment. MRI receiving coil 46 may allow MRI system 42 to be configured to acquire image data from a patient to display an overall image reconstructed using the acquired image data and the acquired position-indicative data (i.e., the induced signal from the MRI tracking coil 32 or 34) which may depict the location of electrode 12 in a patient. MRI receiving coil 46 may be disposed in shaft 10 proximate electrode 12. MM receiving coil 46 may be wound in a substantially cylindrical shape and may have a longitudinal axis that is coincident with longitudinal axis 16 of body 14 of electrode 12. MRI receiving coil 46 may comprise an insulated, electrically conductive wire. MRI receiving coil 46 may comprise copper wire in an embodiment. MRI receiving coil 46 may comprise a superconducting material in another embodiment. A superconducting material may assist in minimizing conductor loss and may offer a better signal to noise ratio (SNR). The strength of a signal is based on the strength of the magnetic field. Stronger magnetic fields may improve the signal, but not be preferred due to the cost of maintaining uniform and stable magnetic fields over the area to be imaged. Accordingly, the SNR may be improved by reducing noise. The contributions to the noise may include both coil noise (e.g., noise to the resistance of the receive coil) and body noise (e.g., noise due to the patient's body). Coil noise may be reduced by reducing the temperature or resistance of the coil. Body noise may be difficult to reduce because generally intravascular (IV) coils contribute to a large body noise. Accordingly, the use of a superconducting material for MRI receiving coil 46 may improve the signal to noise ratio (e.g., by reducing the resistance of the coil) as compared to copper coil, without having to increase the strength of the magnetic field. MRI receiving coil 46 may be configured in accordance with MRI receiving coils known to those of ordinary skill in the art.

A means for tuning or detuning MRI receiving coil 46 may be provided. For example, MRI receiving coil 46 may include two capacitors, each capacitor configured for adjustment. A first capacitor (e.g., matching capacitor) may be used to match the impedance of the MRI receiving coil together with the imaged object to that of the MRI system. The second capacitor (e.g., tuning capacitor) may be used to hold the resonance frequency of the MRI receiving coil to a predetermined value.

In an embodiment, shaft 10 may further include a second tracking device 48 in an embodiment. Second tracking device 48 may be configured in accordance with tracking devices known to those of ordinary skill in the art. Second tracking device 48 may be disposed proximate MRI receiving coil 46. Accordingly MRI tracking coil 32 or 34 and second tracking device 48 may be disposed on opposing sides of MRI receiving coil 46. The second tracking device 48 may comprise an MRI tracking coil and may comprise electrically insulated wire, for example.

Figure 6:
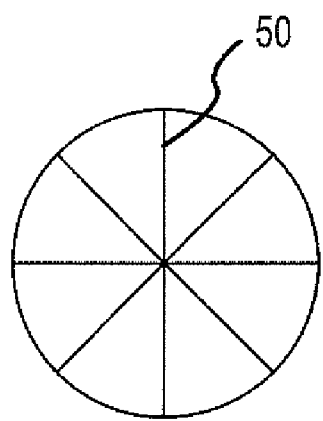
FIG. 6 is an end view of the electrode of FIG. 2 or FIG. 4 in accordance with an embodiment of the invention.
Figure 7:
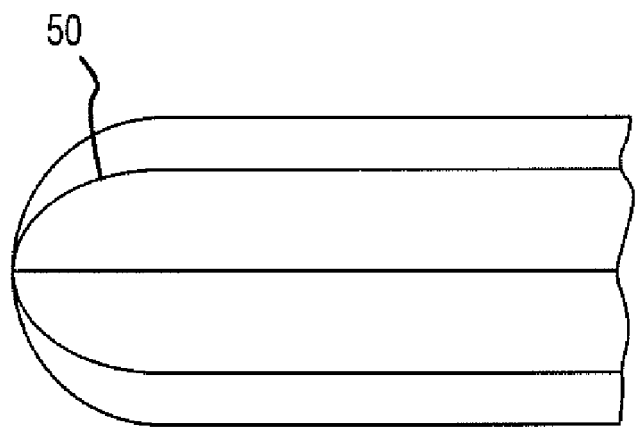
FIG. 7 is a side view of the electrode of FIG. 2 or FIG. 4 in accordance with an embodiment of the invention.

Referring now to FIGS. 6 and 7, at least a distal end 18 of body 14 may include a plurality of slits 50 in an embodiment. Slits 50 may be configured to mitigate and/or reduce the magnitude of potential eddy currents that may form in distal end 18 of body 14. The potential eddy currents may create their own magnetic fields. Without slits 50, the large contiguous mass may create current and subsequent magnetic fields. The sectioning of the distal end 18 of electrode 12 by the inclusion of slits 50 may break up this flow. Slits 50 may be axially extending and may converge to a point on a convex-shaped distal end of body 14 in one embodiment. Although this configuration is described in some detail, slits 50 may be included in various other configurations and/or orientations to facilitate a reduction of the uninterrupted volume susceptible to eddy current formations that may be induced by an MRI system. In an embodiment, an electrically conductive polymer may be disposed in the slits 50 to mitigate edge effects. Slits 50 may be utilized in connection either the first embodiment (see FIG. 2) or the second embodiment (see FIG. 4) of electrode 12.

A method for determining the location of an electrode 12 is also disclosed. The method may include the step of providing an electrode 12 having a main body 14 of electrically conductive material extending along an axis 16 and having a distal end 18 and a proximal end 20. The method may also include the steps of forming a groove in an outermost surface of electrode 12 and disposing an MRI tracking coil 32 or 34 in the groove. MRI tracking coil 32 or 34 may comprise electrically insulated wire, for example. In one embodiment, the method may also include the step of receiving an induced signal developed in MRI tracking coil 32 or 34 at a magnetic resonance imaging (MRI) system 42. The induced signal may be used to depict a location of electrode 12. Image data may also be obtained from a patient using MRI system 42 and an MRI receiving coil 46 disposed in shaft 10, for example. MRI system 42 may also use this image data in displaying an image depicting the location of electrode 12. In another embodiment, the method may include the step of transmitting a magnetic field in order to facilitate tracking of electrode 12 within an MRI system 42. The magnetic field may be transmitted by MRI tracking coil 32 or 34. MRI system 42 may emit an additional excitation pulse (e.g., in addition to the required excitation and relaxation sequence) which would not be used to construct an actual image, but instead to identify the anomaly at the MRI tracking coil 32 or 34 that may be created by the use of MRI tracking coil 32 or 34 as a temporary magnet. The localized anomaly may be used to calibrate the location of the electrode. The imaging protocol of MRI system 42 may include a duty cycle, which is the time permitted during which the gradient (e.g., magnetic gradient field) system can be run at maximum power. In an embodiment, a 50 ms duty cycle may be used, with about 20 ms used for excitation detection and about 30 ms potentially used for tracking electrode 12 through an active emission protocol. The length of the duty cycle may vary in other embodiments.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode assembly for use on a medical device comprising:
   a main body of electrically conductive material extending along an axis and having a proximal end and a distal end, said body configured for connection to a first end of a first electrical conductor and said body being configured to emit electrical energy when a second end of the first electrical conductor is coupled to an energy source;

said body having a groove disposed at least in part over an outermost surface of said body;

a magnetic resonance imaging (MRI) tracking coil disposed in said groove, said MRI tracking coil comprising electrically insulated wire.

2. The electrode assembly of claim 1, wherein said body is configured to emit electrical energy for a radio frequency (RF) ablation function.

3. The electrode assembly of claim 1, wherein said groove comprises a continuous spiral niche.

4. The electrode assembly of claim 3, wherein said niche has a width substantially corresponding to a diameter of said wire.

5. The electrode assembly of claim 1, wherein said groove comprises a single channel having a width large enough to house said MRI tracking coil.

6. The electrode assembly of claim 1, wherein said groove comprises first and second channels, said first channel being axially offset from said second channel by a predetermined distance.

7. The electrode assembly of claim 6, wherein said first and second channels have a width along said axis that is substantially larger than a depth in the radial direction.

8. The electrode assembly of claim 6, wherein said predetermined distance is about 0.5 mm.

9. The electrode assembly of claim 5, wherein said MRI tracking coil has a first segment with a first predetermined number of turns and a second segment with a second predetermined number of turns.

10. The electrode assembly of claim 9, wherein said first segment is disposed in said first channel and said second segment is disposed in said second channel, said first and second segments being electrically series-connected.

11. The electrode assembly of claim 9, wherein said first and second predetermined number of turns is about five.

12. The electrode assembly of claim 1, wherein said body is solid.

13. The electrode assembly of claim 1, wherein said body comprises a non-ferrous material.

14. The electrode assembly of claim 1, wherein said body comprises a gold alloy.

15. The electrode assembly of claim 1, wherein said wire is electrically conductive.

16. The electrode assembly of claim 1, wherein said groove has an entry and an exit and extends a predetermined number of turns from said entry to said exit.

17. The electrode assembly of claim 16, wherein said predetermined number of turns is at least 10 turns.

18. The electrode assembly of claim 1, wherein said groove has a width equal to or less than about 0.5 mm.

19. The electrode assembly of claim 1, wherein said groove has a depth sufficient to receive said MRI tracking coil so that said MRI tracking coil is not disposed externally to said outermost surface of said body of said electrode.

20. The electrode assembly of claim 1, further comprising an electrically conductive polymer disposed in said groove so that an outermost surface of said polymer is substantially flush with said outermost surface of said body of said electrode assembly.

21. The electrode assembly of claim 20, wherein said polymer comprises silicone with gold particles dispersed therein at a predefined density.

22. The electrode assembly of claim 1, wherein said energy source comprises a radio frequency ablation generator.

23. The electrode assembly of claim 1, wherein said MRI tracking coil is configured for developing an induced signal having sufficient information encoded therewith to be indicative of a position of said body of said electrode assembly and to enable a magnetic resonance imaging (MRI) system to depict a location of said body of said electrode assembly in a patient.

24. The electrode assembly of claim 1, wherein said body includes a plurality of slits.

25. A catheter, comprising:
a shaft; and
an electrode assembly disposed on said shaft, said electrode assembly comprising:
a main body of electrically conductive material extending along an axis and having a proximal end and a distal end;
said body having a groove disposed at least in part over an outermost surface of said body;
a magnetic resonance imaging (MRI) tracking coil disposed in said groove, said MRI tracking coil comprising electrically insulated wire; and
an MRI receiving coil configured for MRI imaging disposed in said shaft proximate said electrode assembly, wherein said MRI receiving coil is configured for connection to an MRI system.

26. The catheter of claim 25, said MRI receiving coil comprising electrically conductive wire.

27. The catheter of claim 25, wherein said MRI receiving coil comprises a superconducting material.

28. The catheter of claim 25, further including a means for tuning or detuning said MRI receiving coil.

29. The catheter of claim 25, further including a second MRI tracking coil disposed in said shaft.

30. The catheter of claim 25, further comprising a microcoaxial cable configured for connection to said MRI tracking coil, said cable extending through said shaft.

31. A method of providing an electrode assembly for use on a medical device, comprising:
providing an electrode having a main body of electrically conductive material extending along an axis and having a proximal end and a distal end, said body configured for connection to a first end of a first electrical conductor and said body being configured to emit electrical energy when a second end of the first electrical conductor is coupled to an energy source;
forming a groove in an outermost surface of said body; and
disposing a magnetic resonance imaging (MRI) tracking coil in said groove, said MRI tracking coil comprising electrically insulated wire, wherein said MRI tracking coil is configured for connection to a first end of a second electrical conductor and wherein a second end of the second electrical conductor is configured for connection to a magnetic resonance imaging (MRI) system.

32. The method of claim 31, further comprising:
inducing a signal in said MRI tracking coil; and
receiving said induced signal developed in said MRI tracking coil at said MRI system input.

33. The method of claim 31, further comprising transmitting a magnetic field with said MRI tracking coil, wherein said MRI tracking coil is configured for connection with said MRI system in order to facilitate tracking of said body of said electrode within said MRI system.

34. The electrode assembly of claim 1, wherein said MRI tracking coil is configured for connection to a first end of a second electrical conductor and wherein a second end of the second electrical conductor is configured for connection to a magnetic resonance imaging (MRI) system.

* * * * *